(12) United States Patent
Govari et al.

(10) Patent No.: US 11,484,367 B2
(45) Date of Patent: Nov. 1, 2022

(54) DEVICE AND METHOD OF DETERMINING LOCATION OF SHEATH USING ELECTROMAGNETIC SENSORS ON SHEATH

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Kevin Justin Herrera, West Covina, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 424 days.

(21) Appl. No.: 16/729,284

(22) Filed: Dec. 27, 2019

(65) Prior Publication Data

US 2021/0196394 A1 Jul. 1, 2021

(51) Int. Cl.
*A61B 5/00* (2006.01)
*A61B 34/20* (2016.01)
(Continued)

(52) U.S. Cl.
CPC .............. *A61B 34/20* (2016.02); *A61B 5/062* (2013.01); *A61B 5/065* (2013.01);
(Continued)

(58) Field of Classification Search
CPC ......... A61B 34/20; A61B 5/062; A61B 5/065; A61B 2034/2051; A61B 2034/2053;
(Continued)

(56) References Cited

U.S. PATENT DOCUMENTS

| 5,391,199 A | 2/1995 | Ben-Haim |
| 5,558,091 A | 9/1996 | Acker et al. |

(Continued)

FOREIGN PATENT DOCUMENTS

| EP | 1504713 A1 | 2/2005 |
| WO | WO 96/05768 | 2/1996 |

OTHER PUBLICATIONS

U.S. Appl. No. 16/657,463, filed Oct. 18, 2019.
(Continued)

*Primary Examiner* — Joel Lamprecht
(74) *Attorney, Agent, or Firm* — Volpe Koenig (57) ABSTRACT

A medical tool for use with an electromagnetic navigation system includes a catheter configured to be navigated within patient anatomy and at least one electromagnetic sensor, disposed at the catheter, configured to generate electrical signals indicative of a location of the catheter in response to receiving at least one magnetic field. The medical tool also includes a sheath configured to receive the catheter, a first electromagnetic sensor and a second electromagnetic sensor, disposed at a first region of the sheath, each configured to generate electrical signals indicative of a location of the sheath in response to receiving the at least one magnetic field and a third electromagnetic sensor, disposed at a second region of the sheath spaced from the first region, configured to generate electrical signals indicative of a location of the sheath in response to receiving the at least one magnetic field.

17 Claims, 6 Drawing Sheets

(51) Int. Cl.
    *A61B 5/06* (2006.01)
    *A61M 25/01* (2006.01)
    *A61M 25/06* (2006.01)

(52) U.S. Cl.
    CPC .... *A61M 25/0127* (2013.01); *A61M 25/0133* (2013.01); *A61M 25/0662* (2013.01); *A61B 2034/2051* (2016.02); *A61M 2025/0166* (2013.01)

(58) Field of Classification Search
    CPC ...... A61B 2034/2072; A61M 25/0127; A61M 25/0133; A61M 25/0662; A61M 2025/0166
    See application file for complete search history.

(56) References Cited

U.S. PATENT DOCUMENTS

| | | |
|---|---|---|
| 6,172,499 B1 | 1/2001 | Ashe |
| 6,177,792 B1 | 1/2001 | Govari et al. |
| 6,690,963 B2 | 2/2004 | Ben-Haim et al. |
| 6,788,967 B2 | 9/2004 | Ben-Haim et al. |
| 6,973,339 B2 | 12/2005 | Govari |
| 7,371,232 B2 | 5/2008 | Scheib |
| 7,756,576 B2 | 7/2010 | Levin |
| 7,848,787 B2 | 12/2010 | Osadchy |
| 7,869,865 B2 | 1/2011 | Govari et al. |
| 8,456,182 B2 | 6/2013 | Bar-Tal et al. |
| 8,475,450 B2 | 7/2013 | Govari et al. |
| 8,600,472 B2* | 12/2013 | Govari ................. A61B 5/6856 606/41 |
| 8,608,735 B2 | 12/2013 | Govari et al. |
| 9,050,010 B2 | 6/2015 | Bui et al. |
| 9,220,433 B2 | 12/2015 | Ditter et al. |
| 9,788,893 B2 | 10/2017 | Ditter |
| 9,848,948 B2 | 12/2017 | Fuimaono et al. |
| 2009/0264739 A1 | 10/2009 | Markowitz |
| 2016/0015468 A1* | 1/2016 | Piron .................... A61B 90/39 600/424 |
| 2017/0100188 A1 | 4/2017 | Fang et al. |

OTHER PUBLICATIONS

U.S. Appl. No. 16/198,487, filed Nov. 21, 2018.
U.S. Appl. No. 16/234,604, filed Dec. 28, 2018.
European Search Report for corresponding EPA No. 20217214.4 dated May 20, 2021.

\* cited by examiner

DEVICE AND METHOD OF DETERMINING LOCATION OF SHEATH USING ELECTROMAGNETIC SENSORS ON SHEATH

BACKGROUND

Electromagnetic navigation systems may be utilized to determine a location of a medical tool in three-dimensional (3-D) space within a patient. For example, these electromagnetic navigation systems may include electromagnetic emitters and electromagnetic sensors on the tool to determine the tool's location. Based on the determined location, anatomical information of the patient is displayed to medical personnel.

Some conventional navigation and display systems employ medical tools which include a catheter and a steerable and deflectable (i.e., curvable) sheath. For example, for some medical procedures, such as catheter ablation procedures, the catheter is guided within patient anatomy (e.g., via a blood vessel) through the steerable and deflectable sheath to a target location (e.g., a heart). An example of interaction between a catheter (e.g., balloon catheter) and a sheath is described in U.S. patent application Ser. No. 16/657,463, which is incorporated herein by reference for its teachings on catheter and sheath interaction during a medical procedure.

Because of potential risks associated with x-ray exposure, the sheath is located during these medical procedures without using x-ray. For example, in some conventional systems, the location of the catheter is determined and displayed in a 3D volume using electromagnetic based navigation while the location of the sheath is determined via impedance-based navigation.

SUMMARY

A medical tool for use with an electromagnetic navigation system is provided which includes a catheter configured to be navigated within patient anatomy and at least one electromagnetic sensor, disposed at the catheter, configured to generate electrical signals indicative of a location of the catheter in response to receiving at least one magnetic field. The medical tool also includes a sheath configured to receive the catheter, a first electromagnetic sensor and a second electromagnetic sensor, disposed at a first region of the sheath, each configured to generate electrical signals indicative of a location of the sheath in response to receiving the at least one magnetic field and a third electromagnetic sensor, disposed at a second region of the sheath spaced from the first region, configured to generate electrical signals indicative of a location of the sheath in response to receiving the at least one magnetic field.

A processing device for use with an electromagnetic navigation system is provided which includes memory configured to store data and a processor. The processor is configured to receive location signals from a first electromagnetic sensor disposed at a distal region of a deflectable portion of a sheath of the medical tool, a second electromagnetic sensor disposed at the distal region of the deflectable portion of the sheath, a third electromagnetic sensor disposed at a proximal region of the deflectable portion of the sheath and at least one electromagnetic sensor disposed at a catheter of the medical tool. The processor is also configured to determine a location of the sheath based on the location signals from the first electromagnetic sensor, the location signals from the second electromagnetic sensor and the location signals from the third electromagnetic sensor and determine a location of the catheter based on the location signals from the at least one electromagnetic sensor disposed at the catheter. The location of the sheath and the location of the catheter are displayed.

A method of determining a location of a medical tool in a three-dimensional (3-D) space using an electromagnetic navigation system is provided. The method includes receiving location signals from a first electromagnetic sensor disposed at a distal region of a deflectable portion of a sheath of the medical tool, a second electromagnetic sensor disposed at the distal region of the deflectable portion of the sheath, a third electromagnetic sensor disposed at a proximal region of the deflectable portion of the sheath and at least one electromagnetic sensor disposed at a catheter of the medical tool. The method also includes determining a location of the sheath based on the location signals from the first electromagnetic sensor, the location signals from the second electromagnetic sensor and the location signals from the third electromagnetic sensor and determining a location of the catheter based on the location signals from the at least one electromagnetic sensor disposed at the catheter. The location of the sheath and the location of the catheter are displayed.

BRIEF DESCRIPTION OF THE DRAWINGS

A more detailed understanding can be had from the following description, given by way of example in conjunction with the accompanying drawings wherein.

DETAILED DESCRIPTION

Electromagnetic based navigation is used to determine the location of the catheter in a 3-D volume via electromagnetic emitters and electromagnetic sensors disposed on the catheter. Impedance based navigation is typically used to determine the location of the sheath when the design does not readily support placement of an electromagnetic sensor, such as in the thin wall of a sheath. Impedance based navigation is used to determine the location of the sheath via current emitting rings of the sheath and electrodes with electromagnetic location sensors disposed on the patient (e.g., 6 patch sensors disposed on the patient). Impedance based navigation determines the location of the sheath with less accuracy, however, than the electromagnetic based navigation system determines the location of the catheter. In addition, while impedance-based navigation provides the location of the electrode without yaw, pitch, or roll, a single electromagnetic sensor provides five degrees of freedom (DOF) which include the location as well as yaw and pitch. Further, additional programming is required to correct for location errors of the sheath with respect to the catheter.

The present application discloses a medical navigation system and medical tool for accurately determining the location of a catheter of the medical tool and a location of a sheath of the medical tool during a medical procedure using electromagnetic based navigation. The present application includes a sheath having two or more electromagnetic sensors at a deflectable portion of the sheath to provide six DOF. In one embodiment, the sheath includes two electromagnetic sensors disposed at a distal region of a deflectable portion of the sheath, providing six degrees of freedom at the distal region, and a third electromagnetic sensor disposed at a proximal region of the deflectable portion of the sheath, providing 5 degrees of freedom at the proximal region. The location of the sheath is determined without additional programming used in conventional systems to correct for location errors of the sheath with respect to the catheter.

Figure 1:
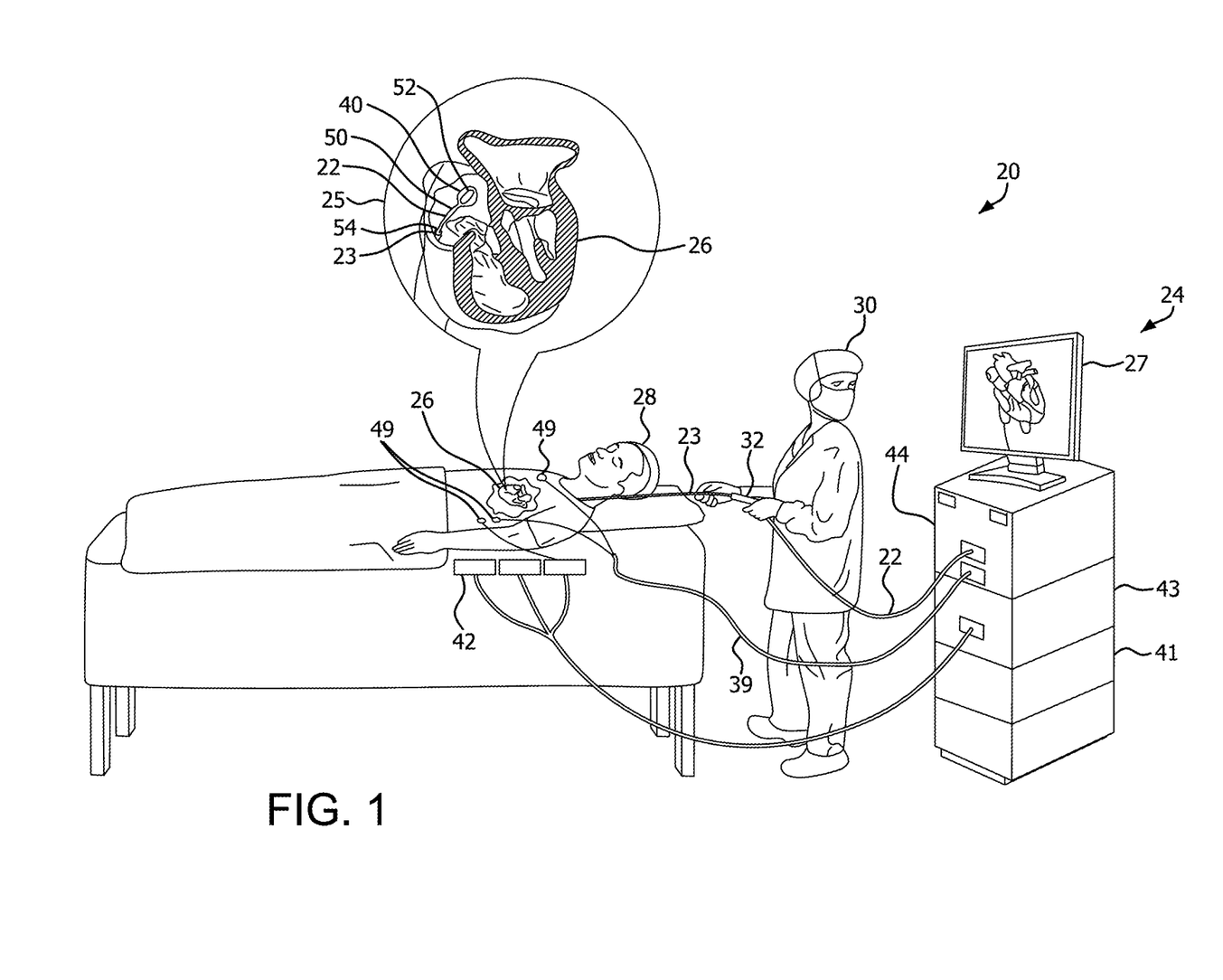
FIG. 1 is a schematic pictorial illustration of an exemplary catheter position tracking system that tracks a catheter inside the heart of a patient, in which exemplary embodiments disclosed herein may be implemented.

FIG. 1 is a schematic pictorial illustration of an example catheter position tracking system 20 that tracks a balloon catheter 40 inside the heart of a patient, in accordance with an embodiment of the present invention. The balloon catheter 40 shown in FIG. 1 is merely an example of a type of catheter in which features of the present application can be implemented. Features of the present application can be implemented using other types of catheters (e.g., basket catheters). The system 20 includes both electric and magnetic position tracking sub-systems. System 20 is used to determine the position of a balloon catheter 40, seen in an inset 25, fitted at a distal end of a shaft 22, and an extent to which the balloon is collapsed before a balloon withdrawal attempt through a sheath 23. Typically, balloon catheter 40 is used for therapeutic treatment, such as spatially ablating cardiac tissue, for example at the left atrium.

Balloon catheter 40 incorporates a proximal position sensor 50 and a distal position sensor 52 fitted on shaft 22, on either side of the balloon. A sheath position sensor 54 is disposed on a distal end of sheath 23 of the catheter. Proximal position sensor 50 and distal position sensor 52 are connected by wires running through shaft 22 to various driver circuitries in a console 24. Sheath position sensor 54, which is disposed at a distal portion of the sheath 23 is connected by wires running initially through sheath 23 and subsequently connected to the various driver circuitries in a console 24.

Typically, proximal position sensor 50, distal position sensor 52, and sheath position sensor 54, comprise either a magnetic sensor or an electrode. The magnetic sensor, or the electrode, is used by the magnetic or electric position tracking sub-systems, respectively, as described below. Physician 30 navigates balloon catheter 40 to a target location in a heart 26 of a patient 28 by manipulating shaft 22 using a manipulator 32 near the proximal end of the catheter and/or deflection from sheath 23. Balloon catheter 40 is inserted, in a collapsed configuration, through sheath 23, and only after sheath 23 is retracted and balloon advancement member is subsequently retracted does balloon catheter 40 regain its intended functional shape. By containing balloon catheter 40 in a folded configuration, sheath 23 also serves to minimize vascular trauma on its way to the target location.

Console 24 comprises a processor 41, typically a general-purpose computer, with suitable front end and interface circuits 44 for receiving signals from various sensors inside and on patient 28.

In some exemplary embodiments, processor 41 accurately determines position coordinates of proximal position sensor 50, distal position sensor 52, and sheath position sensor 54 inside heart 26. Examples of processor coordinate systems may include those used by various position tracking systems, such as the aforementioned electric and magnetic position tracking sub-systems.

In an exemplary embodiment, processor 41 determines the position coordinates, which are based on, among other inputs, measured impedances between an electrode serving as one or more position sensors 50, 52, and 54, and surface electrodes 49. Processor 41 is connected to surface electrodes 49, which are seen in the example system as attached to the skin of patient 28, by wires running through a cable 39 to the chest of patient 28.

The method of electrode position sensing using an electrical position tracking sub-system of system 20 is implemented in various medical applications, for example using the Advanced Catheter Location (ACL) method in the CARTO™ system, produced by Biosense Webster Inc. (Irvine, Calif.) and is described in detail in U.S. Pat. Nos. 7,756,576, 7,869,865, 7,848,787, and 8,456,182, which prior applications are hereby incorporated by reference in its entirety herein into this application.

Using sensed electrode position, a shape of a multi-electrode catheter, such as a balloon catheter, a basket catheter, a LASSO™ or NMARQ™ catheters (both made by Biosense Webster) as well as other multi-electrode deflectable catheters, can be estimated, and a degree of collapse (or straitening) estimated, of a respective expendable, or deflectable, distal end assembly. Examples of a catheter having an end effector in the form of a lasso are shown and described in: U.S. Pat. Nos. 9,788,893; 6,973,339; 8,475,450; 8,600,472; 9,050,010; 9,220,433; 9,848,948; 8,608,735; 7,371,232; and US20170100188, which are all incorporated by reference as if set forth in full herein. Therefore, together with the known distance between a proximal sensor and a sheath sensor, the ACL method can be used with disclosed exemplary embodiments of the invention which do not include a distal position sensor to detect an event in which the expandable distal-end assembly is being withdrawn into the sheath while still at least partially expanded or deflected.

For example, the aforementioned U.S. Pat. No. 8,456,182 with a 'local scaling' process called hereinafter 'Independent Current Location' (ICL) are applicable to catheters having a plurality of sensing-electrodes disposed over their distal end. Using a known spatial relationship among two or more electrodes, e.g., one or more known distances between electrodes, the ICL process can scale the relative positions of a plurality of electrodes so as to exactly estimate a shape of the expendable distal end assembly of the catheter.

In some exemplary embodiments, the disclosed method uses the sheath location sensor and the proximal location sensor with the ACL and ICL derived shape of the expandable distal end assembly to detect an event in which the expandable distal-end assembly is being withdrawn into the sheath while still at least partially expanded or deflected. In such exemplary embodiments, the distal position sensor may be omitted. In general, there can be numerous techniques to estimate the shape of the expandable distal end assembly (and specifically to estimate the extent to which the distal end assembly is expanded). As another example, the shape can be estimated using magnetic position sensors disposed over the expandable distal end assembly. For example, U.S. application Ser. No. 16/198,487, filed Nov. 21, 2018, titled, "Configuring Perimeter of Balloon Electrode as Location Sensor," which is incorporated herein by reference, describes multiple magnetic coils disposed over a balloon to serve as position sensors.

In U.S. application Ser. No. 16/198,487 a spatial configuration of the expandable balloon inside the organ is estimated. It is noted there that the estimating may include estimating at least one of a deflection of the balloon relative to a longitudinal axis defined by the distal end of the shaft and estimating a shape of the balloon inside the organ. The step of estimating a shape may include identifying an extent of expansion of the balloon or detecting whether the balloon is fully expanded or not. In an embodiment, a balloon shape is estimated in a form of an "inflation index," that gives a level of balloon inflation in a dimensionless number. Similarly, an expansion index may be provided with any expandable distal end assembly.

As noted above, system 20 further comprises a magnetic-sensing sub-system. Patient 28 is placed in a magnetic field generated by a pad containing magnetic field generator coils 42, which are driven by unit 43. The magnetic fields generated by coils 42 generate signals in any magnetic position sensor, which are then provided as corresponding electrical inputs to processor 41, which uses these to calculate the position of any of position sensors 50, 52, and 54 that comprise a magnetic sensor.

The method of position sensing using external magnetic fields is implemented in various medical applications, for example, in the CARTO™ system, produced by Biosense Webster Inc., and is described in detail in U.S. Pat. Nos. 5,391,199; 5,558,091; 6,172,499; 6,177,792; 6,788,967 and 6,690,963, and in PCT Patent Publication WO 96/05768, whose disclosures are all incorporated herein by reference.

Using the tracked positions, console 24 may drive a display 27, which shows the distal end of the catheter position inside heart 26. Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables processor 41 to perform the disclosed steps.

FIG. 1 is merely an example system in which embodiments disclosed herein may be implemented. Other electrical-based position measurement systems and methods can be used, such as for example, systems in which voltage gradients are applied between surface electrodes 49 and position signals are derived from the resulting voltage measurements of the intrabody electrodes.

Exemplary techniques for estimating the degree of elongation of an expandable assembly are described in U.S. patent application Ser. No. 16/234,604, filed Dec. 28, 2018, and entitled "Finding Elongation of Expendable Distal End of Catheter," whose disclosure is incorporated herein by reference.

Figure 2:
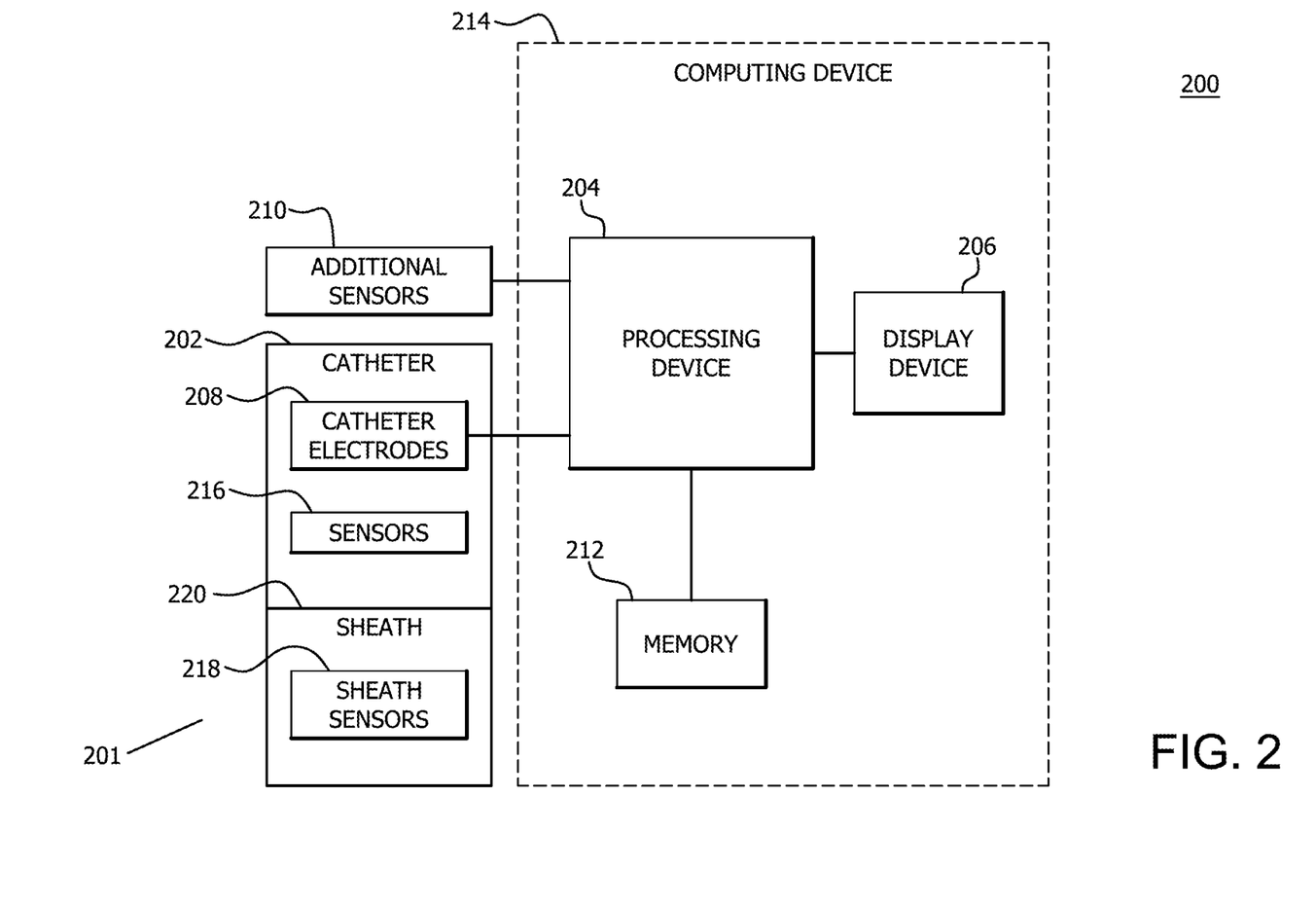
FIG. 2 is an illustration of components of an example electromagnetic navigation system for use with exemplary embodiments described herein.

FIG. 2 is a block diagram illustrating example components of a medical system 200 for use with exemplary embodiments described herein. As shown in FIG. 2, the system 200 includes a medical tool 201, a processing device 204, a display device 206 and memory 212. The medical tool 201 includes a catheter 202 and a sheath 220. The catheter 202 includes catheter electrodes 208 and sensors 216 and is used, for example, to map electrical potentials (e.g., of a heart), ablate portions (e.g., tissue) in patient anatomy or both map electrical potentials and ablate. The sheath 220 is, for example, steerable and deflectable to facilitate, for example, catheter access, stability, and tissue contact in target sites within patient anatomy. For example, during operation the catheter 202 is guided within patient anatomy (e.g., via a blood vessel) through the steerable and deflectable sheath 220 to a target location (e.g., a heart).

As shown in FIG. 2, the processing device 204, display device 206 and memory 212 are a part of an example computing device 214. In some exemplary embodiments, the display device 206 may be separate from computing device 214. Computing device 214 may also include an I/O interface, such as I/O interface 42 shown in FIG. 1.

As shown in FIG. 2, catheter 202 includes one or more sensors 216, which include, for example, magnetic field location sensors (i.e., an electromagnetic sensor) for providing location signals to indicate the 3-D position coordinates of the catheter 202. Sensors 216 can also include, for example, position sensors, pressure or force sensors, temperature sensors, and impedance sensors. The location signals are processed as location data and stored, for example, in memory 212. The processing device 204 receives (e.g., reads from memory) location data corresponding to the location signals and generates mapping information, from the location data, for displaying one or more maps of an organ of interest.

In some exemplary embodiments, sensors 216 can also include sensors used during an ablation procedure to sense ablation parameters, such as for example, catheter position stability, temperature, ablation time, ablation power and ablation impedance during the ablation procedure. In the example shown in FIG. 2, catheter 202 also includes catheter electrodes 208 for mapping electrical potentials of a heart. Catheter 202 may be in wired or wireless communication with processing device 204 to communicate the information acquired by sensors 216.

As shown in FIG. 2, sheath 220 includes sheath sensors 218. For example, as described in more detail below, sheath sensors 218 can include two electromagnetic sensors disposed at a distal region of a deflectable portion of the sheath 220 and a third electromagnetic sensor disposed at a proximal region of the deflectable portion of the sheath 220.

In some exemplary embodiments, one or more additional sensors 210, separate from the medical tool 201, are also used to provide location signals.

Processing device 204 drives display device 206, using the mapping information, to display the map of the organ on display device 206. Display device 206 may include one or more displays each configured to display one or more maps of the organ. For example, display device 206 is configured to display maps representing a spatial-temporal manifestation of an organ (e.g., a heart) as well as geometrical objects which represent estimated ablation depths and widths. Display device 206 may be in wired or wireless communication with processing device 204. In some exemplary embodiments, display device may be separate from computing device 214.

Memory 212 includes, for example, volatile and non-volatile memory, such as random-access memory (RAM), dynamic RAM, or a cache. Memory 212 also includes, for example, storage 214, such as, fixed storage (e.g., a hard disk drive and a solid-state drive) and removable storage (e.g., an optical disk and a flash drive).

Figure 3:
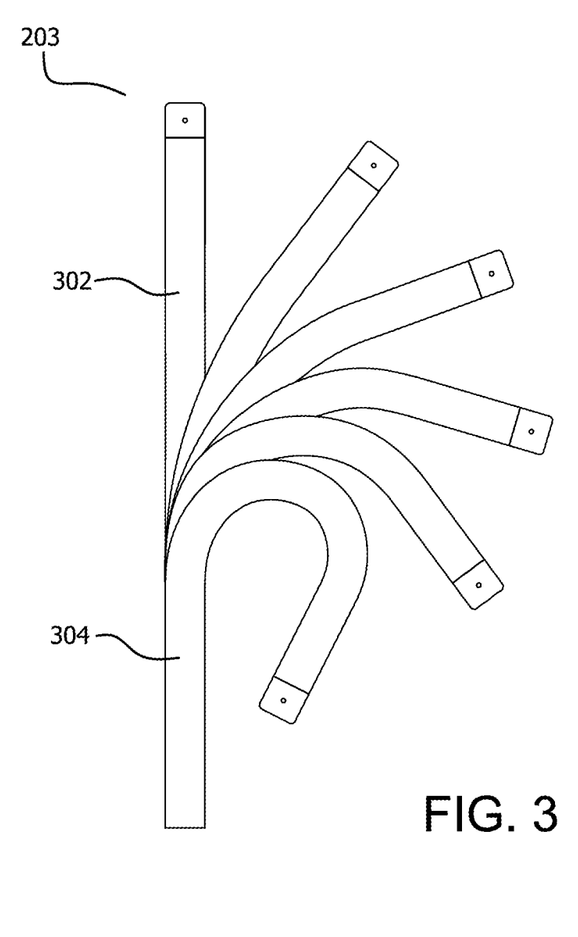
FIG. 3 is an illustration of a part of an exemplary deflectable (i.e., steerable) sheath which can be used to implement exemplary embodiments of the present invention.

FIG. 3 is an illustration of a part of an example deflectable (i.e., steerable) sheath 203 which can be used to implement features of the present disclosure. The sheath 203 is configured to be inserted into and navigated within patient anatomy by an operator (e.g., a physician). A catheter 202 may be guided into a portion (e.g., heart) of patient anatomy through the sheath 203. As shown in FIG. 3, the sheath 203 includes a deflectable portion 302 and a non-deflectable portion 304. Multiple states of the deflectable portion 302 of the sheath 203 are shown in FIG. 3 to illustrate the steerable motion of the sheath 203. Six different states are shown in FIG. 3 for simplification purposes.

Figure 4A:
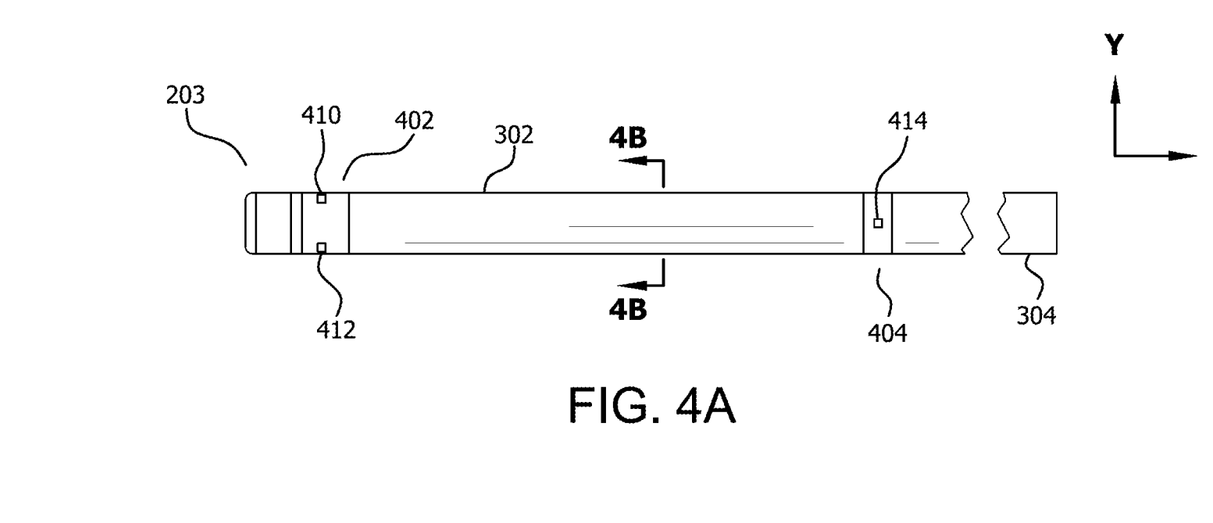
FIG. 4A is a side view of a portion the exemplary sheath in FIG. 3 shown with additional detail.
Figure 4B:
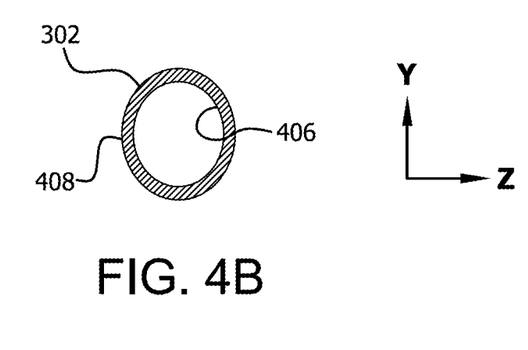
FIG. 4B is cross sectional view along lines A-A of the deflectable portion of the sheath shown in FIG. 4A.

FIG. 4A is a side view of a portion the exemplary sheath 203 in FIG. 3 shown with additional detail. FIG. 4B is cross sectional view along lines A-A of the deflectable portion 302 of the sheath 203 shown in FIG. 4A. As shown in FIG. 4B, the sheath 203 is cylindrical shaped and includes an inner surface 406 and an outer surface 408. The cylindrical shape of the sheath 203 shown in FIG. 4B is merely an example. For simplification purposes, a catheter is not shown in FIGS. 4A and 4B. During operation, however, a catheter 202 is guided through the sheath 203 to a target location (e.g., a heart) within patient anatomy.

As shown in FIG. 4A, the deflectable portion 302 of the sheath 203 includes a distal region 402 and a proximal region 404. To facilitate accurate determination of the location, orientation, and shape of the sheath 203 using electromagnetic based navigation, the sheath's sensors 218 include two separate electromagnetic sensors 410 and 412 disposed at the distal region 402 of the deflectable portion 302 of the sheath 203 and a third electromagnetic sensor 414 disposed at the proximal region 404 of the deflectable portion 302 of the sheath 203. The locations of the distal region 402 and the proximal region 404 shown in FIG. 4A relative to each other are merely examples. In addition, the locations of the distal region 402 and the proximal region 404 shown in FIG. 4A relative to the end of the sheath are also examples. The sensors 410, 412 and 414 are disposed on the sheath such that an approximate distance between the first two sensors and the third sensor includes a distance range of between 10 mm and 150 mm.

In addition, the locations of the electromagnetic sensors 410, 412 and 414 within their corresponding regions 402 and 404 in FIG. 4A are shown for explanation purposes and are merely examples. As described in more detail below with regard to FIG. 5, the sensors 410, 412 and 414 are disposed on the sheath 203 such that their orientations and positions on the sheath 203 provide an accurate determination of the location, orientation, and the curve of the sheath in 3-D space.

Figure 5:
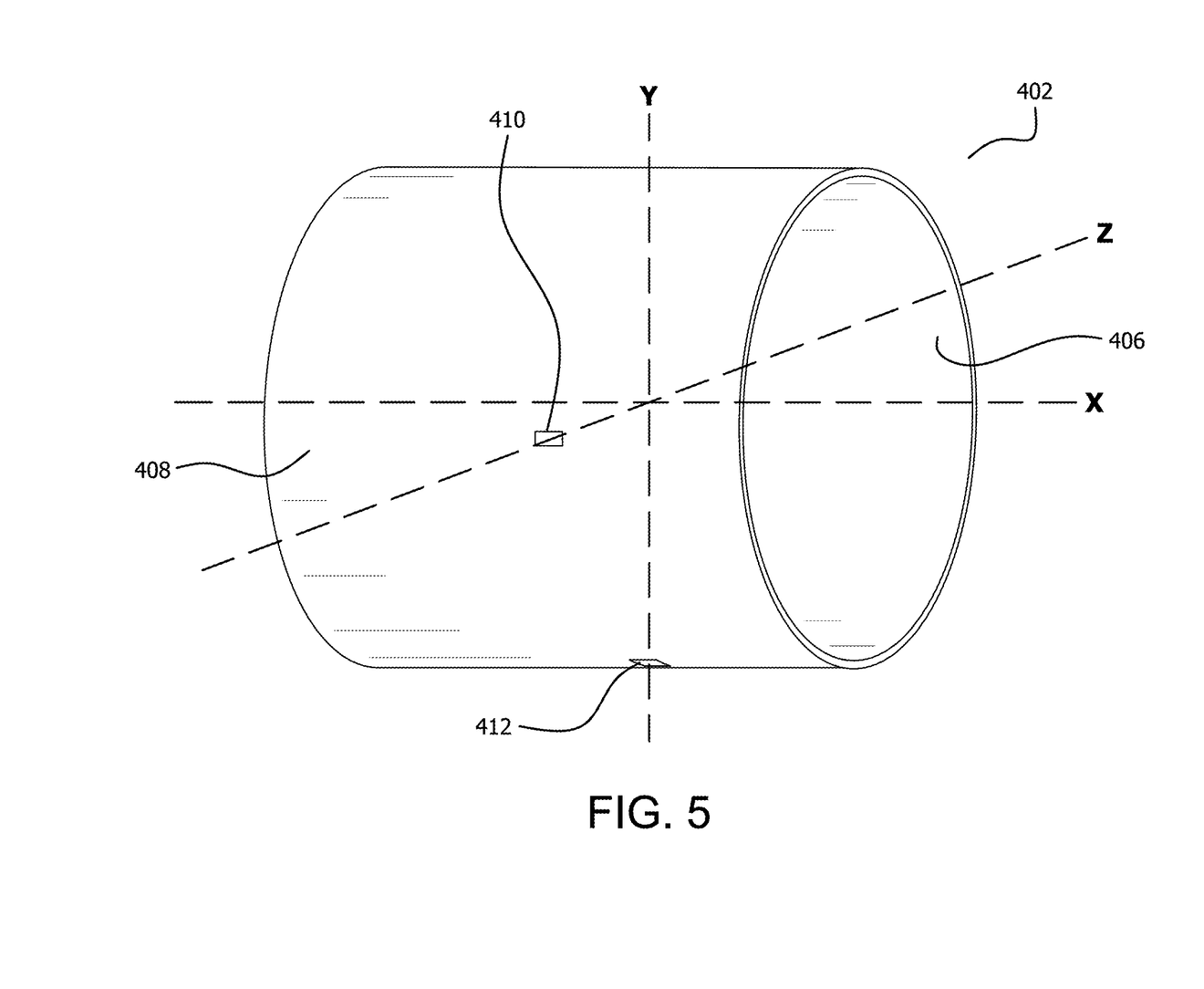
FIG. 5 is a perspective view of the distal region of the deflectable portion of the sheath shown in FIG. 4A.

FIG. 5 is a perspective view of the distal region 402 of the deflectable portion 302 of the sheath 203 shown in FIG. 4A. As shown in FIG. 5, a first electromagnetic sensor 410 is disposed on the outer surface 408 of the sheath 203 at the distal region 402 and a second electromagnetic sensor 412, spaced from the first electromagnetic sensor 410, is disposed at the distal region 402. The electromagnetic sensors 410 and 412 are oriented such that while both are orthogonal to the Z direction, they are not parallel with respect to each other. This allows for a calculation of the full 6 DOF for the assembly comprising sensors 410 and 412. The orientation and location of the electromagnetic sensors 410, 412 and 414 provide 6 DOF at the distal region 402 and 5 DOF at the base, which is enough for accurately determining the location and orientation of the sheath 203 and the curve of the sheath 203.

Figure 6:
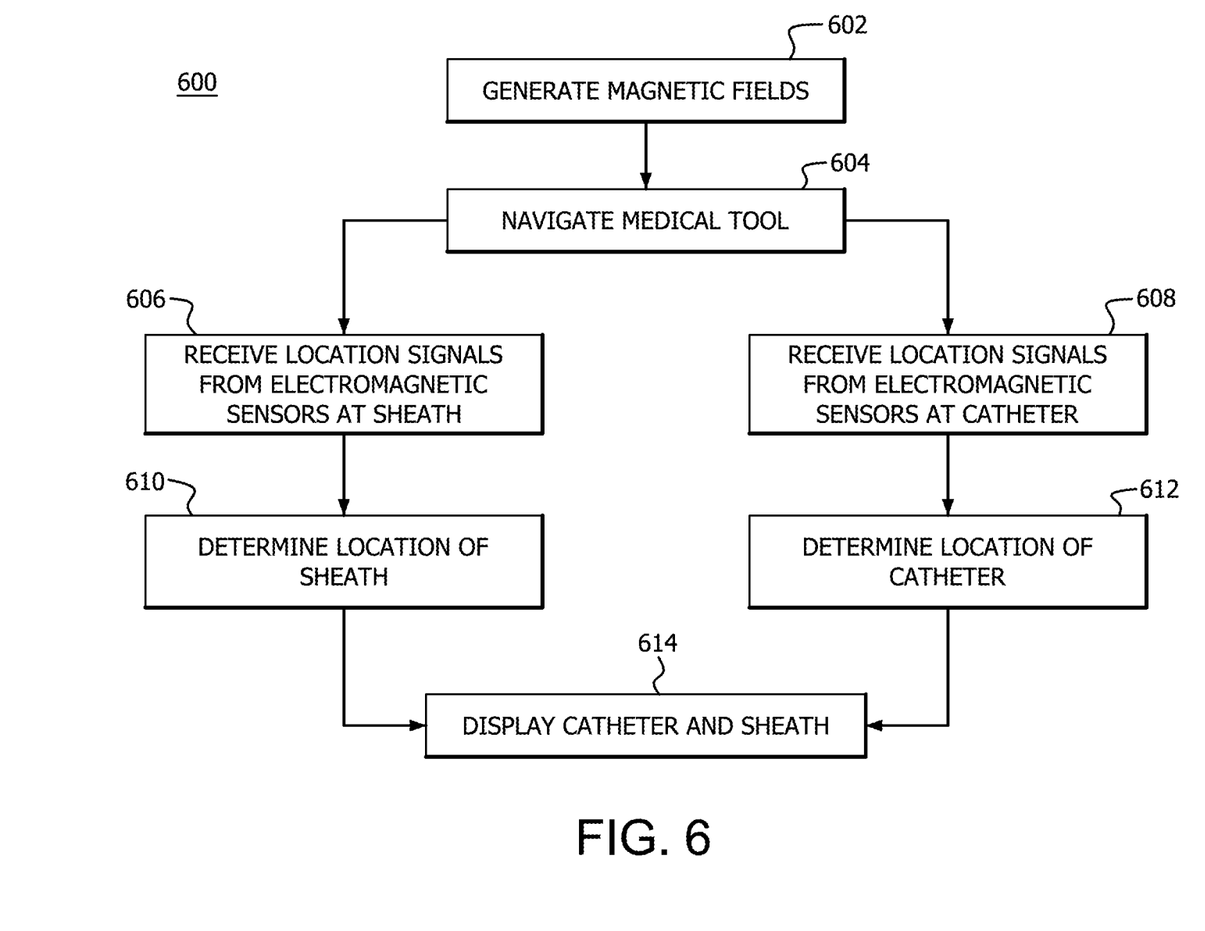
FIG. 6 is a flow diagram illustrating an exemplary method of determining a location of a medical tool in a 3-D space using an electromagnetic navigation system according to an exemplary embodiment of the present invention.

FIG. 6 is a flow diagram illustrating an example method of determining a location of a catheter of a medical tool and a location of a sheath of the medical tool in a 3-D space using an electromagnetic navigation system.

As shown at block 602 of method 600, the method includes generating magnetic fields. For example, field generators, at positions external to a patient, generate magnetic fields in a predefined working volume that contains a portion of interest of the patient anatomy. Each of the emitting coils may be driven by a different frequency to emit a magnetic field in the 3-D space.

As shown at block 604 of method 600, the method includes navigating a medical tool within patient anatomy. For example, during a medical procedure, such as catheter ablation, the medical tool, which includes both the catheter and a steerable sheath, is guided within patient anatomy through the sheath to a target location (e.g., a heart).

As shown at blocks 606-612, the location of the catheter and the sheath are determined using electromagnetic based navigation. As shown at block 606 of method 600, location signals are received from electromagnetic sensor on the sheath. For example, location signals are received from first and second electromagnetic sensors disposed at a distal region of a deflectable portion of a sheath and location signals are received from a third electromagnetic sensor disposed at the proximal region of the deflectable portion of the sheath. As shown at block 608 of method 600, location signals are received from at least one electromagnetic sensor disposed on a catheter of the medical tool. Each of the location signals is generated based on the amplitude and frequency of the magnetic fields to determine the position of the catheter in 3-D space. For example, 3 different magnetic fields (originating from 3 different coils, each operating at a slightly different frequency) are used to triangulate an electromagnetic sensor.

As shown at block 610 of method 600, the method includes determining a location of the sheath based on the location signals received from the first, second and third electromagnetic sensors. As shown at block 612, the method includes determining a location of the catheter based on the location signals received from the at least one electromagnetic sensor disposed at the catheter.

As shown at block 614 of method 600, the method includes displaying the location of the catheter and the sheath. For example, mapping information is generated from each of the location signals and the location of the catheter and sheath are displayed on a display.

The methods provided can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be mask works that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general-purpose computer or a processor. Examples of non-transitory computer-readable storage mediums include a read only memory (ROM), a random-access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. A medical tool for use with an electromagnetic navigation system comprising:
   a catheter configured to be navigated within patient anatomy;
   at least one electromagnetic sensor, disposed on the catheter, configured to provide first electrical signals indicative of a location of the catheter in response to received at least one magnetic field;
   a sheath configured to receive the catheter;
   a first electromagnetic sensor and a second electromagnetic sensor, disposed on a surface of the sheath at a first region of the sheath that is inserted into the anatomy of the patient, configure to provide respective second and third electrical signals indicative of a location of the first region of the sheath within the anatomy of the patient in response to receiving the at least one magnetic field; and
   a third electromagnetic sensor, disposed on the surface of the sheath at a second region of the sheath that is inserted into the anatomy of the patient and spaced from the first region, configured to provide fourth electrical signals indicative of a location of the second region of the sheath within the anatomy of the patient in response to receiving the at least one magnetic field.

2. The medical tool according to claim 1, wherein the first electromagnetic sensor and the second electromagnetic sensor are disposed on the sheath at a distal region of a deflectable portion of the sheath and the third electromagnetic sensor is disposed on the sheath at a proximal region of the deflectable portion of the sheath.

3. The medical tool according to claim 1, wherein the first electromagnetic sensor and the second electromagnetic sensor are oriented such that a first direction, in which the first electromagnetic sensor is sensitive to electromagnetic wave detection, is non-parallel to a second direction, in which the second electromagnetic sensor is sensitive to electromagnetic wave detection.

4. The medical tool according to claim 1, wherein the first electromagnetic sensor and the second electromagnetic sensor are oriented such that a first direction in which the first electromagnetic sensor is sensitive to electromagnetic wave detection, is orthogonal to a second direction, in which the second electromagnetic sensor is sensitive to electromagnetic wave detection.

5. The medical tool according to claim 1, wherein the first electromagnetic sensor and the second electromagnetic sensor provide six degrees of freedom at the distal region of the deflectable portion of the sheath and the third electromagnetic sensor provide five degrees of freedom at the proximal region of the deflectable portion of the sheath.

6. A processing device for use with an electromagnetic navigation system comprising:
   memory configured to store data; and
   a processor configured to:
   receive first location signals from a first electromagnetic sensor disposed on a surface of a sheath at a distal region of a deflectable portion of the sheath that is inserted into an anatomy of a patient, the first electromagnetic sensor configured to receive a catheter of the medical tool;
   receive a second electrical signal from a second electromagnetic sensor disposed on the surface of the sheath at the distal region of the deflectable portion of the sheath that is inserted into the anatomy of the patient;
   receive a third electrical signal from a third electromagnetic sensor disposed on the surface of the sheath at a proximal region of the deflectable portion of the sheath that is inserted into the anatomy of the patient; and
   receive a fourth electrical signal from at least one electromagnetic sensor disposed on the catheter of the medical tool;
   determine a location of the region of the sheath that is inserted into the anatomy of the patient based on the location signals from the first electromagnetic sensor, the location signals from the second electromagnetic sensor and the location signals from the third electromagnetic sensor; and
   determine a location of the catheter based on the location signals from the at least one electromagnetic sensor disposed on the catheter,
   wherein the location of the region of the sheath within the anatomy of the patient and the location of the catheter are each displayed.

7. The processing device of claim 6, wherein the processor is further configured to generate mapping information for displaying the location of the sheath and the location of the catheter.

8. The processing device of claim 6, wherein the processor is further configured to:
   determine a curve of an outer surface of the sheath based on the location signals from the first electromagnetic sensor, the location signals from the second electromagnetic sensor and the location signals from the third electromagnetic sensors, and
   generate mapping information for displaying the location of the sheath and the curve of the sheath.

9. The processing device of claim 6, wherein the first electromagnetic sensor and the second electromagnetic sensor are disposed on the sheath at a distal region of a deflectable portion of the sheath and the third electromagnetic sensor is disposed on the sheath at a proximal region of the deflectable portion of the sheath.

10. The processing device of claim 6, wherein the first electromagnetic sensor and the second electromagnetic sensor are oriented such that a first direction, in which the first electromagnetic sensor is sensitive to electromagnetic wave detection, is non-parallel to a second direction, in which the second electromagnetic sensor is sensitive to electromagnetic wave detection.

11. The processing device of claim 6, wherein the first electromagnetic sensor and the second electromagnetic sensor are oriented such that a first direction, in which the first electromagnetic sensor is sensitive to electromagnetic wave detection, is orthogonal to a second direction, in which the second electromagnetic sensor is sensitive to electromagnetic wave detection.

12. The processing device of claim 6, wherein the first electromagnetic sensor and the second electromagnetic sensor provide six degrees of freedom at the distal region of the deflectable portion of the sheath and the third electromagnetic sensor provide five degrees of freedom at the proximal region of the deflectable portion of the sheath.

13. A method of determining a location of a medical tool in a three-dimensional (3-D) space using an electromagnetic navigation system, the method comprising:
   receiving first location signals from a first electromagnetic sensor disposed on a surface of a sheath at a distal region of a deflectable portion of the sheath that is inserted into an anatomy of a patient, the sheath configured to receive a catheter of the medical tool;
   receiving second location signals from a second electromagnetic sensor disposed on the surface of the sheath at the distal region of the deflectable portion of the sheath that is inserted within the anatomy of the patient;
   receiving third location signals from a third electromagnetic sensor disposed on the surface of the sheath at a proximal region of the deflectable portion of the sheath that is inserted within the anatomy of the patient; and
   receiving fourth location signals from at least one electromagnetic sensor disposed on the catheter of the medical tool;
   determining a location of the region of the sheath within the anatomy of the patient based on the first location signals from the first electromagnetic sensor, the second location signals from the second electromagnetic sensor and the third location signals from the third electromagnetic sensor; and
   determining a location of the catheter based on the location signals from the at least one electromagnetic sensor disposed on the catheter t,
   wherein the location of the region of the sheath within the anatomy of the patient, and the location of the catheter are each displayed.

14. The method of claim 13, wherein the first electromagnetic sensor and the second electromagnetic sensor are oriented such that a first direction, in which the first electromagnetic sensor is sensitive to electromagnetic wave detection, is non-parallel to a second direction, in which the second electromagnetic sensor is sensitive to electromagnetic wave detection.

15. The method of claim 13, wherein the first electromagnetic sensor and the second electromagnetic sensor are oriented such that a first direction, in which the first electromagnetic sensor is sensitive to electromagnetic wave detection, is non-parallel to a second direction, in which the second electromagnetic sensor is sensitive to electromagnetic wave detection.

16. The method of claim 13, wherein the first electromagnetic sensor and the second electromagnetic sensor are oriented such that a first direction, in which the first electromagnetic sensor is sensitive to electromagnetic wave detection, is orthogonal to a second direction, in which the second electromagnetic sensor is sensitive to electromagnetic wave detection.

17. The method of claim 13, wherein the first electromagnetic sensor and the second electromagnetic sensor provide six degrees of freedom at the distal region of the deflectable portion of the sheath and the third electromagnetic sensor provides five degrees of freedom at the proximal region of the deflectable portion of the sheath.

* * * * *

UNITED STATES PATENT AND TRADEMARK OFFICE
CERTIFICATE OF CORRECTION

PATENT NO. : 11,484,367 B2
APPLICATION NO. : 16/729284
DATED : November 1, 2022
INVENTOR(S) : Assaf Govari et al.

It is certified that error appears in the above-identified patent and that said Letters Patent is hereby corrected as shown below:

In the Specification

In Column 2, Line 42, delete "portion the" and insert -- portion of the --, therefor.
In Column 2, Line 67, delete "than the" and insert -- the --, therefor.
In Column 7, Line 11, delete "portion the" and insert -- portion of the --, therefor.
In Column 8, Line 60, delete "computer readable" and insert -- computer-readable --, therefor.

In the Claims

In Column 11, Line 31, in Claim 13, delete "catheter t" and insert -- catheter --, therefore.

Signed and Sealed this
Twenty-second Day of July, 2025

Coke Morgan Stewart
*Acting Director of the United States Patent and Trademark Office*